United States Patent [19]

Reiser et al.

[11] Patent Number: 4,929,735
[45] Date of Patent: May 29, 1990

[54] PROCESS FOR THE PREPARATION OF OXIRANES

[75] Inventors: Wolf Reiser, Wuppertal; Peter Feyen, Mettmann, both of Fed. Rep. of Germany

[73] Assignee: Bayer Aktiengesellschaft, Leverkusen, Fed. Rep. of Germany

[21] Appl. No.: 185,211

[22] Filed: Apr. 22, 1988

Related U.S. Application Data

[63] Continuation of Ser. No. 921,712, Oct. 20, 1986, abandoned.

[30] Foreign Application Priority Data

Oct. 24, 1985 [DE] Fed. Rep. of Germany ....... 3537817

[51] Int. Cl.$^5$ ................... C07D 301/04; C07D 405/06
[52] U.S. Cl. ................... 548/268.8; 549/519; 549/551; 549/554
[58] Field of Search ............. 548/262; 549/519, 551, 549/554

[56] References Cited

U.S. PATENT DOCUMENTS

| | | | |
|---|---|---|---|
| 4,162,258 | 7/1979 | Higo et al. | 568/819 |
| 4,499,281 | 2/1985 | Holmwood et al. | 548/262 |
| 4,532,341 | 7/1985 | Holmwood et al. | 549/559 |
| 4,626,595 | 12/1986 | Holmwood et al. | 549/559 |
| 4,632,999 | 11/1986 | Zerbes et al. | 549/519 |

FOREIGN PATENT DOCUMENTS

| | | | |
|---|---|---|---|
| 3315619 | 10/1984 | Fed. Rep. of Germany | 549/519 |
| 3315681 | 10/1984 | Fed. Rep. of Germany | 549/519 |

OTHER PUBLICATIONS

Chemical Abstracts, vol. 102, 149006P No. 17, Apr. 29, 1985.
Chemical Abstracts, vol 96, 103999U No. 13, Mar. 29, 1982.
Chemical Abstracts, vol. 82, 30900d No. 5, Feb. 3, 1975.
Mosset et al., "Trimethylsulfonium, etc." CA 104:68688b (1986).
Kutsuma et al., "A Convenient Method, etc." Heterocycles 8, 1977, 397-401.

Primary Examiner—Richard L. Raymond
Assistant Examiner—Patricia L. Morris
Attorney, Agent, or Firm—Sprung, Horn, Kramer & Woods

[57] ABSTRACT

A process for the preparation of an oxirane of the formula

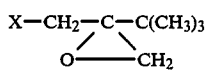

in which
X is 4-chlorobenzyl, 4-phenylphenoxy or 1H-(1,2,4)-triazolyl,
comprising reacting dimethyl sulphate with an excess of dimethyl sulphide thereby to form trimethylsulphonium methyl-sulphate of the formula

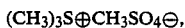

and without prior isolation reacting the trimethylsulphonium methyl-sulphate with a keytone of the formula

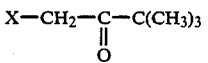

in the presence of solid potassium hydroxide or sodium hydroxide in dimethyl sulphide at a temperature between 0° C. and 50° C.

6 Claims, No Drawings

PROCESS FOR THE PREPARATION OF OXIRANES

This is a continuation of application Ser. No. 921,712, filed Oct. 20, 1986 now abandoned.

The present invention relates to a new process for the preparation of known oxiranes which can be used as intermediate products for the synthesis of compounds with a plant growth-regulating and fungicidal activity.

It has already been disclosed that oxiranes can be prepared by reacting dimethyl sulphide with dimethyl sulphate and then reacting the trimethylsulphonium methylsulphate thereby formed as an intermediate with carbonyl compounds in the presence of an inert organic solvent and in the presence of a strong base, such as butyllithium, sodium hydride, sodium amide, potassium tert.-butylate, sodium methylate or sodium ethylate (compare J. Amer. Chem. Soc. 87, 1363–1364 (1965) and Ber. 96, 1881 (1963)). Thus, for example, 2-(4-chlorophenoxy-methyl)-2-tert.butyloxirane can be prepared by reacting trimethylsulphonium methyl-sulphate, prepared from dimethyl sulphide and dimethyl sulphate, in situ with 1-(4-chlorophenoxy)-3,3-dimethyl-butan-2-one in acetonitrile in the presence of sodium methylate (compare EP-OS (European Published Specification) 40,345). The yields in this process are good. A disadvantage is, however, that the bases used must in each case be prepared specifically and are difficult to handle, since they are sensitive to moisture and in some cases also combustible. The fact that relatively long reaction times are necessary both in the preparation of the trimethylsulphonium methyl-sulphate and in its subsequent reaction with the ketone also impedes the process.

It is furthermore known that oxiranes are obtained when dimethyl sulphide is treated with dimethyl sulphate and the trimethylsulphonium methyl-sulphate thereby obtained is reacted with carbonyl compounds in the presence of concentrated aqueous sodium hydroxide solution, an organic solvent of low water-miscibility and in the presence of a phase transfer catalyst (compare Angew. Chem. 85, 867–868 (1973) and J. Org. Chem. 34, 2133 (1969)). However, only aldehydes have hitherto been converted into oxiranes by this process. Furthermore, the presence of a phase transfer catalyst is necessary in each case in the system consisting of two liquid phases.

Finally, it is already known that oxiranes can be synthesized by treating dimethyl sulphide with dimethyl sulphate in the presence of an inert organic solvent, such as, for example, acetonitrile, and reacting the trimethylsulphonium methyl-sulphate thereby formed, without prior isolation, with certain ketones in the presence of solid potassium hydroxide or sodium hydroxide and in the presence of an inert organic solvent, such as, for example, toluene (compare U.S. Ser. No. 603,478, filed Apr. 24, 1984, now pending, corresponding to German Published Specification) DE-OS 3,315,619). The yields of the desired products are very good. A decisive disadvantage of this process, however, is that relatively long reaction times are required in each case both in the preparation of the trimethylsulphonium methyl-sulphate and in its reaction with a ketone.

It has now been found that the known oxiranes of the formula

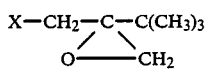
(I)

in which
X represents 4-chlorobenzyl, 4-phenylphenoxy or 1H-(1,2,4)-triazolyl,
are obtained by a process in which dimethyl sulphate is treated with an excess of dimethyl sulphide and the trimethylsulphonium methyl-sulphate thereby formed, of the formula

(II)

is reacted, without prior isolation, with a ketone of the formula

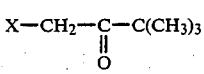
(III)

in which
X has the abovementioned meaning,
in the presence of solid potassium hydroxide or sodium hydroxide in dimethyl sulphide if appropriate in the presence of a polar aprotic diluent, at temperatures between 0° C. and 50° C.

It is to be described as extremely surprising that oxiranes of the formula (I) can be prepared in an extremely high yield by the process according to the invention in substantially shorter reaction times than in the case of the processes known from EP-OS (European Published Specification) 0,040,345 and U.S. Ser. No. 603,478, filed Apr. 24, 1984, corresponding to German Published Specification) DE-OS 3,315,619.

The process according to the invention is distinguished by a number of advantages. Thus, the bases which can be used are also available on an industrial scale, are easy to handle and are non-combustible. Furthermore, the dimethyl sulphide present in excess, which functions both as the reaction component and as the diluent, can be recovered without difficulty and used again in further reactions. Since this is a low-boiling diluent here, the amounts of energy required for warming to the reaction temperature and for recycling are relatively low.

The simple working up of the reaction mixture obtained after the reaction is also of advantage. Polar aprotic diluent which may be contained in the reaction mixture passes completely into the aqueous phase during working up. It should also be mentioned that the oxiranes of the formula (I) are obtainable in a very high yield by the process according to the invention.

If 1-(4-chlorophenyl)-4,4-dimethylpentan-3-one is used as the starting substance and solid potassium hydroxide is used as the base in the process according to the invention, the course of the reaction can be illustrated by the following equation:

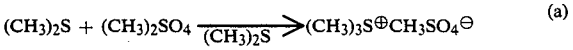
(a)

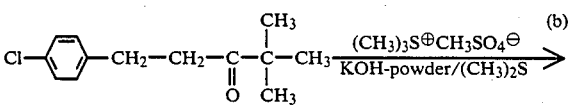
(b)

-continued

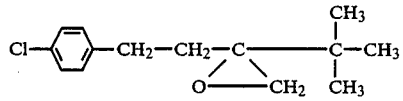

Formula (III) provides a definition of the ketones required as starting substances in the process according to the invention. In this formula, X represents 4-chlorobenzyl, 4-phenylphenoxy or 1H-(1,2,4)-triazolyl.

Examples of ketones of the formula (III) which may be mentioned are those substances which are listed below by way of their formulae:

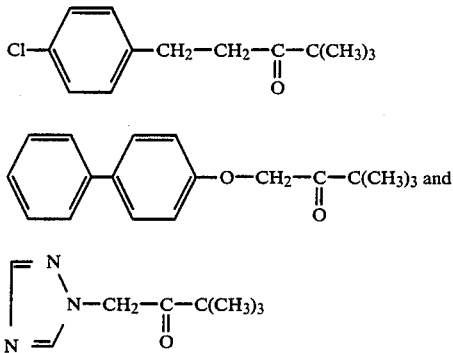

The ketones of the formula (III) are already known (compare DE-OS (German Published Specification) 3,315,619, DE-OS (German Published Specification) 3,315,681 and U.S. Pat. No. 4,499,281, issued Feb. 12, 1985, corresponding to (German Published Specification) DE OS 3,111,238.

The trimethylsulphonium methyl-sulphate of the formula (II) furthermore required as a starting substance in the process according to the invention is likewise known (compare Heterocycles 8, 397 (1977)). It is employed in the above reaction in the freshly prepared state, in that it is produced in situ by reaction of dimethyl sulphide with dimethyl sulphate.

Bases which are used in the process according to the invention are potassium hydroxide or sodium hydroxide in solid form. They can be employed as pellets or powders.

Dimethyl sulphide functions as the diluent in the process according to the invention, and in particular both in the preparation of the trimethylsulphonium methylsulphate and in subsequent reactions thereof with a ketone of the formula (III). However, it is also possible to use dimethyl sulphide mixed with a polar aprotic solvent, such as N-methylpyrrolidone, dimethylformamide or dimethylsulphoxide, as the diluent.

The reaction temperatures can be varied within a certain range in carrying out the process according to the invention. The reaction is in general carried out at temperatures between 0° C. and 50° C. both in the preparation of the trimethylsulphonium methyl-sulphate and in the subsequent reaction thereof with a ketone of the formula (III). Preferably, the preparation of the trimethylsulphonium methyl-sulphate is carried out at temperatures between 20° and 40° C. and subsequent reaction of the salt with a ketone of the formula (III) is carried out at temperatures between 15° C. and 40° C., which corresponds to the reflux temperature of the solvent.

The process according to the invention is carried out under normal pressure.

The reaction times in the process according to the invention are in general between 1 and 16 hours, preferably between 1.5 and 8 hours.

In carrying out the process according to the invention, the amounts of reaction components and diluents are chosen so that in general 2 to 15 moles, preferably 3 to 10 moles, of dimethyl sulphide and in general 1 to 3 moles, preferably 1.2 to 2.0 moles, of dimethyl sulphate and in general 1 to 6 moles, preferably 1.5 to 4 moles, of potassium hydroxide or sodium hydroxide are employed per mole of ketone of the formula (III).

In detail, the reaction by the process according to the invention is carried out by a procedure in which dimethyl sulphate is brought together with an excess of dimethyl sulphide, a solution of ketone of the formula (III) in dimethyl sulphide, if appropriate mixed with a polar aprotic solvent, is then added to this mixture and the particular desired amount of base is subsequently added. Working up is carried out by customary methods. In general, a procedure is followed in which water is added to the reaction mixture, the phases are separated, the organic phase is neutralized by addition of dilute mineral acid, the phases are separated and the organic phase is washed with water and concentrated by distilling off the diluent under normal pressure. The product thereby obtained can be distilled under reduced pressure for further purification.

The oxiranes of the formula (I) which can be prepared by the process according to the invention are useful starting substances for the synthesis of 1-hydroxyethylazole derivatives, which have outstanding plant growth-regulating and fungicidal properties (compare EP-OS (European Published Specification) 0,040,345 and U.S. Pat. No. 4,548,945, issued Oct. 22, 1985, corresponding to (German Published Specification) DE-OS 3,237,400.

Thus, for example, 1-(4-chlorophenyl)-3-(1,2,4-triazol-1-yl-methyl)-4,4-dimethyl-pentan-3-ol can be prepared by reacting 2-(4-chlorophenyl-ethyl)-2-tert.-butyl-oxirane with 1,2,4-triazole in the presence of sodium hydroxide. The synthesis can be represented by the following equation:

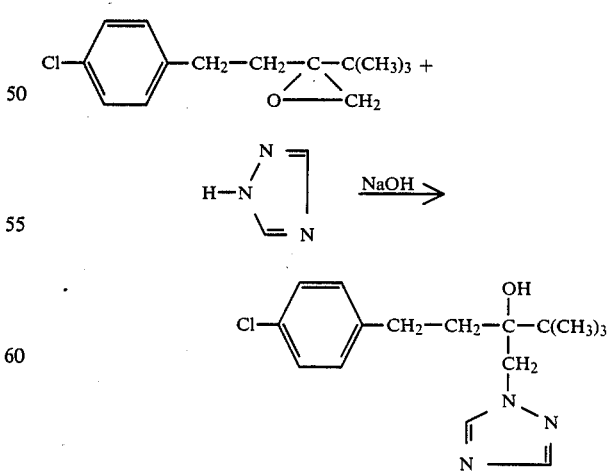

Furthermore, 3,3-dimethyl-2-(4-methoximinomethyl-phenoxymethyl)-1-(1,2,4-triazol-1-yl)-butan-2-ol can be prepared by reacting 2-(1,2,4-triazol-1-yl-methyl)-2- tert.-butyl-oxirane with 4-methoximinomethyl-phenol in the presence of potassium carbonate. This synthesis can be represented by the following equation:

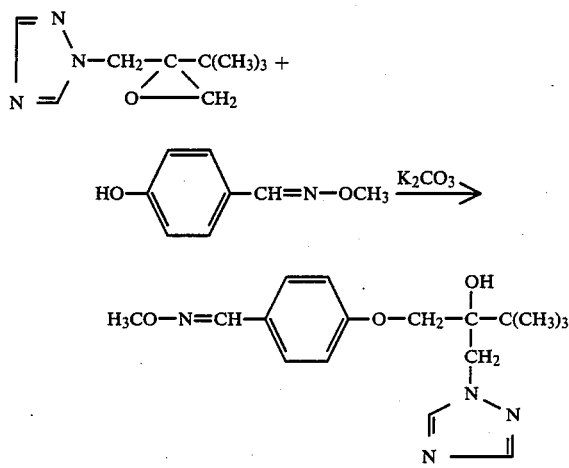

The process according to the invention and the preparation of end products from the oxiranes of the formula (I) are illustrated by the following examples.

EXAMPLE 1

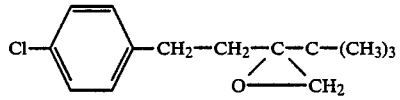

378.4 g (3 moles) of dimethyl sulphate were added dropwise to a mixture of 744 g (12 moles) of dimethyl sulphide, 72.5 ml of dimethylsulphoxide and 453.2 g (2 moles) of 1-(4-chlorophenyl)-4,4-dimethyl-pentan-3-one at 30° C., while stirring, so that the reaction mixture warmed to 40° C. When the addition had ended, the mixture was subsequently stirred at 40° C. for 2 hours and then cooled to 18° C., and 448 g (7 moles) of potassium hydroxide powder were added in portions, whereupon the reaction mixture warmed to 27° C. The mixture was then stirred at 40° C. for a further 3 hours. According to the gas chromatogram, the content of 2-(4-chlorophenyl-ethyl)-2-tert.-butyl-oxirane in samples taken from the reaction mixture was 70.5% one hour after the addition of potassium hydroxide, 89.8% after 2 hours and 94.3% after 3 hours.

EXAMPLE 2

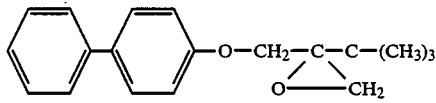

75.6 g (0.6 mole) of dimethyl sulphate were added dropwise to 186 g (3 moles) of dimethyl sulphide at 40° C. in the course of 20 minutes, while stirring. The mixture was then stirred at room temperature for a further 2 hours. After subsequent addition of 11.3 ml of dimethylsulphoxide and 134 g (0.5 mole) of 1-(4-phenyl-phenoxy)-3,3-dimethylbutan-2-one, 56 g (0.9 mole) of potassium hydroxide powder were added in portions. According to the gas chromatogram, the content of 1-(4-phenyl-phenoxy-methyl)-2-tert.butyl-oxirane in the samples taken from the reaction mixture after the addition of the potassium hydroxide was 86.6% after 1 hour and 95.9% after 2 hours.

200 ml of water were then added to the mixture. The organic phase was separated off and neutralized with dilute aqueous hydrochloric acid. The organic phase was separated off again and then washed with water and concentrated by distillation under normal pressure. 128.3 g of a residue which, according to the gas chromatogram, consisted of 1-(4-phenyl-phenoxymethyl)-2-tert.-butyl-oxirane to the extent of 92.8% were obtained.

EXAMPLE 3

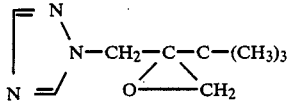

163.8 g (1.3 moles) of dimethyl sulphate were added dropwise to 592 g (9.55 moles) of dimethyl sulphide at a temperature of 36° C. in the course of 2 hours, while stirring. After the reaction mixture had been stirred at 36° C. for four hours, it was cooled to room temperature and 167 g (1 mole) of 1-(1H-1,2,4-triazolyl)-3,3-dimethyl-butan-2-one and 95.45 g (1.5 moles) of potassium hydroxide powder were added in succession. According to the gas chromatogram, the content of 2-[(1H)-(1,2,4-triazolylmethyl]-2-tert.-butyl-oxirane in the samples taken from the reaction mixture after the addition of potassium hydroxide was 73.9% after 0.5 hour and 79.5% after 3 hours.

COMPARISON EXAMPLE

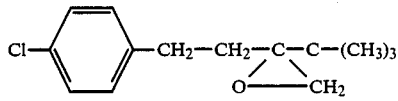

18.9 g (0.3 mole) of dimethyl sulphide were added dropwise to a mixture of 88 ml of toluene, 22 ml of dimethylsulphoxide and 38 g (0.3 mole) of dimethyl sulphate, while stirring, whereupon the temperature of the mixture rose to 52° C. The mixture was subsequently stirred at room temperature for a further 4 hours and 46.8 g (0.2 mole) of 1-(4-chlorophenyl)-4,4-dimethylpentan-3-one were then added. 44.8 g (0.7 mole) of potassium hydroxide powder were then added, whereupon the temperature of the mixture was kept at 40° C. by cooling. Thereafter, the mixture was cooled to room temperature. According to the gas chromatogram, the content of 2-(4-chlorophenyl-ethyl)-2-tert.-butyl-oxirane in the samples removed from the reaction mixture after the addition of potassium hydroxide was 57.5% after 1.5 hours, 65.0% after 3 hours and 92.1% after 20 hours.

Examples for the use of oxiranes prepared according to the invention for the synthesis of 1-hydroxyethylazole derivatives with a fungicidal and plant growth-regulating activity:

EXAMPLE A

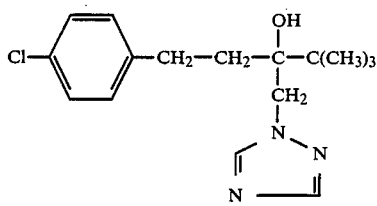

5.3 g (0.05 mole) of sodium carbonate were added to a mixture of 245.2 g (1 mole) of 2-(4-chlorophenylethyl)-2-tert.-butyl-oxirane (97.2% pure), 72.5 g (1 mole) of 1,2,4-triazole (95.2% pure) and 380 ml of dimethylsulphoxide at room temperature, while stirring, and the mixture was then heated at 110° C. for 4 hours. Thereafter, the reaction mixture was poured into 1 liter of water and neutralized with dilute aqueous hydrochloric acid. The liquid phase was decanted off from the solid and the residue was dissolved in 1 liter of toluene. The solution was extracted with water, the phases were separated and the organic phase was dried and concentrated by stripping off the diluent under reduced pressure. 128 g (42% of theory) of 1-(4-chlorophenyl)-3-(1,2,4-triazol-1-ylmethyl)-4,4-dimethyl-pentan-3-ol were obtained in this manner in the form of a solid.

EXAMPLE B

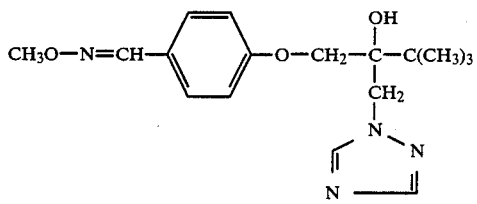

A mixture of 151.0 g (1 mole) of 4-methoximinomethyl-phenol (100% pure), 222.3 g (1 mole) of 2-(1,2,4-triazol-1-yl-methyl)-2-tert.-butyl-oxirane (81.7% pure) and 13.8 g (0.1 mole) of ground potassium carbonate in 500 ml of dimethysulphoxide was heated at 110° C. for 24 hours and then concentrated under reduced pressure. 500 ml of isopropanol were added to the residue, 600 ml of water were added dropwise and the mixture was cooled to 5° C. After addition of seed crystals, the mixture was stirred at room temperature for 16 hours and the precipitate which had separated out was then filtered off. This residue was washed with 250 ml of 50% strength aqueous isopropanol and then dried. 270.3 g of a product which, according to the gas chromatogram, consisted of 3,3-dimethyl-2-(4-methoximino-methyl-phenoxymethyl)-1-(1,2,4-triazol-1-yl)-butan-2-ol to the extent of 80.1% were obtained in this manner. The yield is accordingly calculated as 65.1% of theory.

It will be understood that the specification and examples are illustrative but not limitative of the present invention and that other embodiments within the spirit and scope of the invention will suggest themselves to those skilled in the art.

We claim:

1. A process for the preparation of an oxirane of the formula

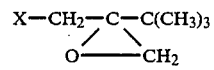

in which
X is 4-chlorobenzyl, 4-phenylphenoxy or 1H-(1,2,4)-triazolyl,
comprising reacting dimethyl sulphate with an excess of dimethyl sulphide thereby to form trimethylsulphonium methyl-sulphate of the formula

and without prior isolation reacting the trimethylsulphonium methyl-sulphate with a ketone of the formula

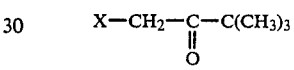

in the presence of solid potassium hydroxide or sodium hydroxide in dimethyl sulphide at a temperature between 0° C. and 50° C., 2 to 15 moles of dimethyl sulphide, 1 to 3 moles of dimethyl sulphate and 1 to 6 moles of potassium hydroxide or sodium hydroxide being employed per mole of ketone.

2. The process according to claim 1, wherein the reaction of dimethyl sulphate with dimethyl sulphide is carried out at the boiling point of the dimethyl sulphide.

3. The process according to claim 1, wherein the reaction of the trimethylsulphonium methyl-sulphate with the ketone is carried out at a temperature between 20° C. and 40° C.

4. The process according to claim 1, wherein the ketone is 1-(4-chlorophenyl)-4,4-dimethyl-pentan-3-one.

5. The process according to claim 1, wherein the ketone is 1-(4-phenyl-phenoxy-3,3-dimethyl-butan-2-one.

6. The process according to claim 1, wherein the ketone is 1-(1H)-(1,2,4-triazolyl)-3,3-dimethyl-butan-2-one.

* * * * *